(12) United States Patent
Backman et al.

(10) Patent No.: US 8,735,075 B2
(45) Date of Patent: May 27, 2014

(54) CANCER SCREENING BY DETECTION OF ULTRASTRUCTURAL AND MOLECULAR MARKERS

(75) Inventors: Vadim Backman, Chicago, IL (US); Hariharan Subramanian, Chicago, IL (US); Dhwanil Damania, Evanston, IL (US); Hemant Roy, Highland Park, IL (US); Dhananjay Kunte, Vernon Hills, IL (US); Mart De La Cruz, Niles, IL (US)

(73) Assignees: Northwestern University, Evanston, IL (US); Northshore University Healthsystem, Evanston, IL (US)

( * ) Notice: Subject to any disclaimer, the term of this patent is extended or adjusted under 35 U.S.C. 154(b) by 51 days.

(21) Appl. No.: 13/399,706

(22) Filed: Feb. 17, 2012

(65) Prior Publication Data

US 2012/0214880 A1 Aug. 23, 2012

Related U.S. Application Data

(60) Provisional application No. 61/443,912, filed on Feb. 17, 2011.

(51) Int. Cl.
*C12Q 1/68* (2006.01)
*G01N 1/28* (2006.01)

(52) U.S. Cl.
USPC .............. 435/6.14; 435/4; 435/29; 435/40.51

(58) Field of Classification Search
None
See application file for complete search history.

(56) References Cited

U.S. PATENT DOCUMENTS

| 7,667,832 B2 | 2/2010 | Backman et al. |
| 7,800,746 B2 | 9/2010 | Backman et al. |
| 2010/0257618 A1 | 10/2010 | Croce et al. |

OTHER PUBLICATIONS

Ahlquist et al. "Stool DNA and occult blood testing for screen detection of colorectal neoplasia," Ann Intern Med, 149(7): 441-450, W481, 2008.
Bernstein et al. "Field defects in progression to gastrointestinal tract cancers," Cancer Lett, 260(1-2): 1-10, 2008.
Brenner et al. "Mass screening with CT colonography: should the radiation exposure be of concern?," Gastroenterology, 129(1): 328-337, 2005.
Brenner et al. "Risk of progression of advanced adenomas to colorectal cancer by age and sex: estimates based on 840,149 screening colonoscopies," Gut, 56(11): 1585-1589, 2007.
Dakubo et al. "Clinical implications and utility of field cancerization," Cancer Cell International, 7(2): 2007.
Davidson et al. "n-3 Polyunsaturated fatty acids modulate carcinogen-directed non-coding microRNA signatures in rat colon," Carcinogenesis, 30(12): 2077-2084, 2009.
Dhruva et al. "CMS's landmark decision on CT colonography—examining the relevant data," N Engl J Med, 360 (26):2699-2701, 2009.
Duffy et al. "Clinical utility of biochemical markers in colorectal cancer: European Group on Tumour Markers (EGTM) guidelines," Eur J Cancer, 39(6): 718-727, 2003.
Hewiston et al. "Cochrane systematic review of colorectal cancer screening using the fecal occult blood test (hemoccult): an update," Am J Gastroenterol, 103(6): 1541-1549, 2008.
Huang et al. "Plasma microRNAs are promising novel biomarkers for early detection of colorectal cancer," Int J Cancer, 127(1): 118-126, 2010.
Hundt et al. "Comparative evaluation of immunochemical fecal occult blood tests for colorectal adenoma detection," Ann Intern Med, 150(3): 162-169, 2009.
Imperiale et al. "Fecal DNA versus fecal occult blood for colorectal-cancer screening in an average-risk population," New Engl J Med, 351(26): 2704-2714, 2004.
International Search Report and Written Opinion for International Application No. PCT/US2012/025670, mailed May 31, 2012.
Johnson et al. "Accuracy of CT colonography for detection of large adenomas and cancers," N Engl J Med, 359(12): 1207-1217, 2008.
Kahi et al. "Effect of screening colonoscopy on colorectal cancer incidence and mortality," Clin Gastroenterol Hepatol, 7(7): 770-775; quiz 711, 2009.
Kimberly et al. "Extracolonic findings at virtual colonoscopy: an important consideration in asymptomatic colorectal cancer screening," J Gen Intern Med, 24(1): 69-73, 2009.
Konishi et al. "Concordant DNA methylation in synchronous colorectal carcinomas," Cancer Prev Res, 2(9): 814-822, 2009.
Kopelovich et al. "Surrogate anatomic/functional sites for evaluating cancer risk: an extension of the field effect," Clin Cancer Res, 5(12): 3899-3905, 1999.
Leman et al. "Initial analyses of colon cancer-specific antigen (CCSA)-3 and CCSA-4 as colorectal cancer-associated serum markers," Cancer Res, 67(12): 5600-5605, 2007.
Levin et al. "Screening and surveillance for the early detection of colorectal cancer and adenomatous polyps, 2008: a joint guideline from the American Cancer Society, the US Multi-Society Task Force on Colorectal Cancer, and the American College of Radiology," Gastroenterology, 134(5): 1570-1595, 2008.
Lieberman et al. "Clinical practice. Screening for colorectal cancer," N Engl J Med, 361(12):1179-1187, 2009.
Lynch et al. "Hereditary colorectal cancer," N Engl J Med, 348(10): 919-932, 2003.

(Continued)

*Primary Examiner* — James Martinell
(74) *Attorney, Agent, or Firm* — Perkins Coie LLP

(57) ABSTRACT

The present invention relates to detection of cancer, or assessment of risk of development thereof. In particular, the present invention provides compositions and methods detection of field carcinogenesis by identification of ultrastructural and molecular markers in a subject.

16 Claims, 8 Drawing Sheets

(56) References Cited

OTHER PUBLICATIONS

Matsushita et al. "A new method for isolating colonocytes from naturally evacuated feces and its clinical application to colorectal cancer diagnosis," Gastroenterology, 129(6): 1918-1927, 2005.
Mensink et al. "Change in anatomic distribution and incidence of colorectal carcinoma over a period of 15 years: clinical considerations," Dis Colon Rectum, 45(10): 1393-1396, 2002.
Nagel et al. "Regulation of the adenomatous polyposis coli gene by the miR-135 family in colorectal cancer," Cancer Res, 68(14): 5795-5802, 2008.
National Cancer Institute. Colon Cancer Treatment, Sep. 24, 2009, retrieved from http://web.archive.org/web/20090924131514/http://www.cancer.gov/cancertopics/pdq/treatment/colon/Patient/page5, on May 13, 2012.
Nosho et al. "A prospective cohort study shows unique epigenetic, genetic, and prognostic features of synchronous colorectal cancers," Gastroenterology, 137(5): 1609-1620, 2009.
Rabeneck et al. "Bleeding and perforation after outpatient colonoscopy and their risk factors in usual clinical practice," Gastroenterology, 135(6): 1899-1906, 1906.e1, 2008.
Regge et al. "Diagnostic accuracy of computed tomographic colonography for the detection of advanced neoplasia in individuals at increased risk of colorectal cancer," JAMA, 301(23): 2453-2461, 2009.
Rockey et al. "Analysis of air contrast barium enema, computed tomographic colonography, and colonoscopy: prospective comparison," Lancet, 365(9456): 305-311, 2005.
Roy et al. "Down-regulation of SNAIL suppresses MIN mouse tumorigenesis: modulation of apoptosis, proliferation, and fractal dimension," Mol Cancer Ther, 3(9): 1159-1165, 2004.
Roy et al. "Four-dimensional elastic light-scattering fingerprints as preneoplastic markers in the rat model of colon carcinogenesis," Gastroenterology, 126(4): 1071-1081, 2004.
Seeff et al. "How many endoscopies are performed for colorectal cancer screening? Results from CDC's survey of endoscopic capacity," Gastroenterology, 127(6): 1670-1677, 2004.
Seeff et al. "Is there endoscopic capacity to provide colorectal cancer screening to the unscreened population in the United States?," Gastroenterology, 127(6): 1661-1669, 2004.
Shah et al. "Management of small polyps detected by screening CT colonography: patient and physician preferences," Am J Med, 122(7), 687 e1-9, 2009.
Slaby et al. "MicroRNAs in colorectal cancer: translation of molecular biology into clinical application," Mol Cancer, 8: 102, 2009.
Subramanian et al. "Nanoscale cellular changes in field carcinogenesis detected by partial wave spectroscopy," Cancer Res, 69(13): 5357-5363, 2009.
Subramanian et al. "Optical methodology for detecting histologically unapparent nanoscale consequences of genetic alterations in biological cells," Proc Natl Acad Sci USA, 105(51): 20118-20123, 2008.
Subramanian et al. "Partial-wave microscopic spectroscopy detects subwavelength refractive index fluctuations: an application to cancer diagnosis," Optics Letters, 34(4): 518-520, 2009.
Tazawa et al. "Tumor-suppressive miR-34a induces senescence-like growth arrest through modulation of the E2F pathway in human colon cancer cells," Proc Natl Acad Sci USA, 104(39): 15472-15477, 2007.
U.S. Preventative Services Task Force "Screening for Colorectal Cancer: U.S. Preventative Services Task Force Recommendation Statement," Ann Intern Med, 149(9): 627-637, 2008.
Valeri et al. "Modulation of mismatch repair and genomic stability by miR-155," Proc Natl Acad Sci USA, 107(15): 6982-6987, 2010.
Van Gossum et al. "Capsule endoscopy versus colonoscopy for the detection of polyps and cancer," N Engl J Med, 361(3): 264-270, 2009.
Warren et al. "Adverse events after outpatient colonoscopy in the Medicare population," Ann Intern Med, 150(12): 849-857, W152, 2009.
White et al. "Isolation of stool-derived mucus provides a high yield of colonocytes suitable for early detection of colorectal carcinoma," Cancer Epidemiol Biomarkers Prev, 18(7): 2006-2013, 2009.
Whitlock et al. "Screening for colorectal cancer: a targeted, updated systematic review for the U.S. Preventive Services Task Force," Ann Intern Med, 149(9): 638-658, 2008.
Winawer et al. "Prevention of colorectal cancer by colonoscopic polypectomy. The National Polyp Study Workgroup," N Engl J Med, 329(27): 1977-1981, 1993.

Fig. 3. Mucus layer fecal colonocytes isolated from control and AOM rat stool

| Saline vs. AOM (uninvolved mucosa) | | Saline vs. tumor (uninvolved mucosa) | | AOM vs. tumor | |
|---|---|---|---|---|---|
| Increase | Decrease | Increase | Decrease | Increase | Decrease |
| 6 | 0 | 87 | 19 | 76 | 14 |

(b)

| Marker | AUC |
|---|---|
| Ld | 0.8765 |
| miR-34a | 0.9375 |
| Ld + miR-34a | 1.0000 |

CANCER SCREENING BY DETECTION OF ULTRASTRUCTURAL AND MOLECULAR MARKERS

GOVERNMENT INTERESTS

This invention was made with government support under Grant Nos. R01 CA128641, U01 CA111257, and R21 CA156944 awarded by the National Institutes of Health, and Grant No. CBET-0937987 awarded by the National Science Foundation. The government has certain rights in the invention.

CROSS REFERENCE TO RELATED APPLICATIONS

This application claims the benefit of and priority to U.S. Provisional Application No. 61/443,912, filed on Feb. 17, 2011, the entire disclosure of which is hereby incorporated by reference in its entirety.

FIELD OF THE INVENTION

The present invention relates to detection of cancer, or assessment of risk of development thereof. In particular, the present invention provides compositions and methods for detection of field carcinogenesis by identification of ultrastructural and molecular markers in a subject.

BACKGROUND OF THE INVENTION

In 2009, there were 146,970 new cases of colorectal cancer (CRC) in the U.S. resulting in 49,920 deaths (Jemal et al. CA Cancer J Clin 59(4), 225-249 (2009).; herein incorporated by reference in its entirety). The lifetime risk of an American developing CRC is ~5.3%. Screening the asymptomatic population can prevent 65-90% of all CRCs through both diagnosis and removal of the precursor lesion, the adenomatous polyp. Unfortunately, ~50% of the population does not undergo any screening due to concerns about cost, discomfort, complications, embarrassment, and availability. Thus, more effective screening strategies are needed. CRC screening approaches include stool, blood, radiographic and endoscopic (Lieberman. N Engl J Med 361(12), 1179-1187 (2009).; Whitlock et al. Ann Intern Med 149(9), 638658 (2008).; herein incorporated by reference in their entireties). The Multi-group Task Force recommends two classes of CRC tests: tests that target only carcinomas (e.g. stool tests) and those that are also sensitive to adenomas. The latter is strongly advocated given its potential for cancer prevention through interruption of the adenoma-carcinoma sequence (Levin et al. Gastroenterology 134(5), 1570-1595 (2008).; herein incorporated by reference in its entirety). The US Preventive Services Task Force recommends only stool tests (FOBT, not DNA), flexible sigmoidoscopy and colonoscopy ("Screening for Colorectal Cancer: U.S. Preventive Services Task Force Recommendation Statement," Ann Intern Med (2008).; herein incorporated by reference in its entirety). Flexible sigmoidoscopy (endoscopic examination of the distal colon) was a stalwart of CRC screening, but has lost favor due to inability to detect proximal neoplasia (particularly important in women) (Seeff et al. Gastroenterology 127(6), 1670-1677 (2004).; Mensink et al. Dis Colon Rectum 45(10), 1393-1396 (2002).; herein incorporated by reference in their entireties). Air-contrast barium enema is infrequently used given advent of more sensitive, less uncomfortable tests (Rockey et al. Lancet 365(9456), 305-311 (2005).; herein incorporated by reference in its entirety). Serum tests include proteomic, antibody arrays, or specific proteins (TIMP-1, CCSA-3 and CCSA-4), but lack sensitivity for advanced adenomas (Duffy et al. Eur J Cancer 39(6), 718-727 (2003).; Leman et al. Cancer Res 67(12), 5600-5605 (2007).; herein incorporated by reference in their entireties). Recent multi-center trials reported that for significant neoplasia (>10 mm), virtual colonoscopy (CT colography or CTC) had per lesion sensitivities of 84% and 80% in average and high-risk cohorts, respectively (Johnson et al. N Engl J Med 359(12), 1207-1217 (2008).; Regge et al. Jama 301 (23), 2453-2461 (2009).; herein incorporated by reference in their entireties). However, the CTC miss rate for CRCs was not trivial (~6%). Moreover, it is impractical to refer all patients for colonoscopy for lesions identified by CTC because of cost and patient satisfaction (logistic constraints require a second visit and bowel purge for colonoscopy). However, leaving potentially premalignant lesions in place is unpalatable for most patients and physicians (Shah et al. Am J Med 122(7), 687 e681-689 (2009).; herein incorporated by reference in its entirety). Other concerns include discomfort (due to bowel purge for CTC and colonic air insufflation), radiation exposure from serial examinations, and management of extra-intestinal findings on CTC, which occur in 66% of cases with 16% deemed to require further investigation (Brenner & Georgsson. Gastroenterology 129(1), 328-337 (2005).; Kimberly et al. J Gen Intern Med 24(1), 69-73 (2009).; herein incorporated by reference in their entireties). These and other concerns led the Center for Medicare Studies to decide against reimbursing the CTC (Dhruva. et al. N Engl J Med 360(26), 2699-2701 (2009).; herein incorporated by reference in its entirety). Imaging capsule (PiliCam) has recently received considerable attention. However, this approach still needs bowel purge, is expensive, and requires a second procedure if a polyp is identified. A recent study showed poor performance for advanced adenomas (sensitivity 73% and specificity 79%) and cancers (sensitivity 74%) (Van Gossum et al. N Engl J Med 361 (3), 264-270 (2009).; herein incorporated by reference in its entirety). Colonoscopy is the most accurate test (98% sensitivity for advanced adenomas) and has been demonstrated to reduce future neoplasia by an estimated 65-90% (Winawer et al. N Engl J Med 329(27), 1977-1981 (1993).; herein incorporated by reference in its entirety).

Colonoscopy will likely remain the "gold standard" of screening for the foreseeable future. The combination of diagnostic and therapeutic capabilities is particularly attractive. Unfortunately, utilizing colonoscopy for screening the entire population is impractical. There is insufficient capacity to perform colonoscopy on the entire average risk population (over 100 million Americans over age 50) (Kahi et al. Clin Gastroenterol Hepatol7(7), 770-775; quiz 711 (2009).; Seeff et al. Gastroenterology 127(6), 1661-1669 (2004).; herein incorporated by reference in their entireties). Even if there were capacity, the cost would be prohibitive (estimates up to $50 billion per year). Complications from colonoscopy are not rare, including life-threatening issues such as bleeding or bowel perforation especially in the elderly (Rabeneck et al. Gastroenterology 135(6), 1899-1906, 1906 e1891 (2008).; Warren et al Ann Intern Med 150(12), 849-857, W152 (2009).; herein incorporated by reference in their entireties). These limitations are juxtaposed with the remarkably low yield of screening relevant neoplasia (~5-7%). Thus, in retrospect, more than 90% colonoscopies could possibly be deemed unnecessary.

Fecal tests for CRC screening are a minimally invasive and highly desirable option. The main advantage is excellent patient acceptability since non-compliance with invasive screening is the major problem with current CRC screening. Existing fecal tests rely on detecting consequences of tumors such as bleeding or tumor products. Indeed, the fecal occult blood test (FOBT) is widely used but is unable to detect advanced adenomas, the target of CRC screening efforts. Indeed, guaiac and even more accurate immunohistochemical techniques (Hemoccult and Hemoccult Sensa) have sensitivities between 11-21%; a stool DNA panel improved sensitivity to only 18-20% despite a marked increase in cost ($400-700 per test) (2008 study in 4,482 patients) (Imperiale et al. N Engl J Med 351 (26), 2704-2714 (2004).; Ahlquist et al Ann Intern Med 149(7), 441-450, W481 (2008).; Hewitson et al. Am J Gastroenterol 103(6), 1541-1549 (2008).; herein incorporated by reference in their entireties). Thus, better fecal tests are urgently needed (Levin et al. Gastroenterology 134(5), 1570-1595 (2008).; herein incorporated by reference in its entirety).

Feces are composed of apoptotic intestinal epithelial cells (the entire lining is shed every 3-7 days), bacteria and remnants of food. There has been interest in isolating fecal colonocytes from the fecal mucus layer through immunomagnetic bead purification. However, this is expensive and cumbersome (Matsushita et al. Gastroenterology 129(6), 1918-1927 (2005).; herein incorporated by reference in its entirety). Recently, it was shown that the mucus layer of stool contains morphologically viable, non-apoptotic colonocytes. While typical fecal assays have looked for tumor cells (the "needle in a haystack" limitation), the mucus layer colonocytes are more likely to come from the normal colonocytes (abraded from the epithelium as formed stool scrapes against mucosa) (White et al. Cancer Epidemiol Biomarkers Prev 18(7), 2006-2013 (2009).; herein incorporated by reference in its entirety). Thus, the existing fecal tests are subject to the "needle in a haystack" limitation and have unacceptably poor sensitivity, especially for early curable lesions. What is needed is a fecal test for detection of CRC that is capable of early detection and does not rely on bleeding or tumor products.

A common theme in a variety of malignancies (e.g., colon, lung, head and neck, liver, etc.) is field carcinogenesis (also known as field effect, field defect or field of injury), the observation that the genetic/environmental milieu that results in colon carcinogenesis diffusely impacts upon the entire colonic mucosa (Kopelovich et al. Clin Cancer Res 5(12), 3899-3905 (1999).; Roy et al. Gastroenterology 126(4), 1071-1081 (2004).; Bernstein et al. Cancer Lett 260(1-2), 1-10 (2008).; herein incorporated by reference in their entireties). The hallmark is the clinical observation of synchronous and metachronous lesions, which frequently share similar genetic/epigenetic characteristics. (Nosho et al. Gastroenterology (2009).; Konishi et al. Cancer Prev Res (Phila Pal 2(9), 814-822 (2009).; herein incorporated by reference in their entireties).

MicroRNAs (miRNAs or miRs) are small non-coding, 18-25 nucleotides long RNAs that down-regulate gene expression through binding and degrading mRNA. There has been a major interest in miRNAs and cancer. Dysregulation of ~700 miRNAs has been implicated in carcinogenesis generally via epigenetic silencing of tumor suppressor genes/proto-oncogenes (Valeri et al. Proc Natl Acad Sci USA 107(15), 6982-6987 (2010).; herein incorporated by reference in its entirety). The role in early carcinogenesis is emphasized by the fact that ~50% of miRNAs are located in fragile areas of the chromosome(s) (deletion/amplifications) (Slaby et al. Mol Cancer 8, 102 (2009).; herein incorporated by reference in its entirety). In CRC, miRNAs modulate many critical genetic pathways (e.g. EGFR (AKT, PI-3 kinase), p53, IGF-1, COX-2, epithelial-mesenchymal transition, angiogenesis and invasion). Thus, miRNAs are critical to the entire spectrum of CRC. Given their critical role, miRNAs may serve as an early detection target (Huang et al. Int J Cancer 127(1), 118-126 (2010).; herein incorporated by reference in its entirety). Combined ROC analyses using miR-29a and miR-92a showed AUC of 0.88 and 0.77 for identifying patients with CRC vs. advanced adenomas (Hundt et al Ann Intern Med 150(3), 162-169 (2009).; herein incorporated by reference in its entirety). There are two major pathways of colon carcinogenesis; the chromosomal instability (CIN), initiated by mutations in APC, and the mismatch repair (MMR) enzymes (most commonly hMLH and hMSH2). Importantly, both APC and MMR gene expression is regulated by miRs (miR-135 and miR-155) (Valeri et al. Proc Natl Acad Sci USA 107(15), 6982-6987 (2010).; Nagel et al. Cancer Res 68(14), 5795-5802 (2008).; herein incorporated by reference in their entireties). Data from the AOM-treated rat model suggest that miRNAs may be modulated in field carcinogenesis (Davidson et al. Carcinogenesis 30(12), 2077-2084 (2009).; herein incorporated by reference in its entirety).

While the above background most directly applies to colorectal cancer, the same considerations and implications apply to other cancers, and methods of screening. Indeed, as a biological phenomenon, field carcinogenesis has been described in multiple types of cancer.

SUMMARY OF THE INVENTION

The present invention relates to detection of cancer, or assessment of risk of development thereof. In particular, the present invention provides systems and methods for the detection of field carcinogenesis through the selection of particularly suitable cell types and markers.

In some embodiments, field carcinogenesis may be utilized for screening of a number of major types of cancer (e.g., colon, lung, prostate, ovarian, etc.). In certain embodiments, a tissue specimen is obtained from an part of an organ (e.g., an easily accessible portion) that is at risk for harboring or developing a neoplastic, cancerous, or precancerous lesion (e.g., by cell brushing), from a surrogate site that is not part of the organ but shares field carcinogenesis with the organ, or from a byproduct of a function of the organ, such as its natural or stimulated secretions (e.g., fecal matter, urine, saliva, secretions). In particular embodiments, the cells in the tissue specimen are not from a tumor and appear histologically normal according to the conventional criteria of histopathology. However, in some embodiments, the cells in the tissue specimen exhibit markers of field carcinogenesis (e.g., ultrastructural (nanoarchitectural), optical, and/or molecular (microRNA) markers). In some embodiments, markers are identified by optical, molecular, and/or other analyses to identify whether a subject has field carcinogenesis. In certain embodiments, if field carcinogenesis is detected, this is indicative of an cancer, pre-cancer, or increased risk of harboring or developing a precancerous or cancerous lesion in that organ. In some embodiments, the present application provides a combination of ultrastructural (a.k.a. nanoarchitectural) markers detected (e.g., by means of optical techniques such as partial wave spectroscopy (PWS) and PWS microscopy) and molecular markers (e.g., alterations in microRNA expression) as a diagnostic of field carcinogenesis. In particular embodiments, the present application provides a combination of ultrastructural (a.k.a. nanoarchitectural) markers detected (e.g., by means of optical techniques such as partial wave spectroscopy (PWS) and PWS microscopy) and molecular markers (e.g., alterations in microRNA expression) as a synergistic analysis that provides a more accurate diagnosis than the markers individually.

In some embodiments, combined ultrastructural and molecular analysis finds use in the analysis of buccal epithelial cells obtained by brushing from the oral cavity for the assessment of lung cancer risk, analysis of cervical epithelial cells for assessment of the risk of ovarian cancer, analysis of upper esophageal epithelial cells for assessment of the risk of esophageal adenocarcinoma, and analysis of duodenal epithelial cells for analysis of the risk of pancreatic cancer, etc. the scope of the invention is not limited by these applications. In some embodiments, the present invention provides a fecal test for CRC, pre-CRC, or increased risk of CRC that does not rely on bleeding or tumor products for detection. In some embodiments, mucus layer colonocytes are identified in the stool and the markers of field carcinogenesis are detected. In some embodiments, markers of field carcinogenesis include, but are not limited to PWS nanocytology and microRNA analysis. In some embodiments, detection of the field effect, a diffuse phenomenon that affects most of colonic epithelial cells, significantly increases the probability of detecting abnormal cells in the stool, thus dramatically improving test sensitivity over existing tests.

In some embodiments, the present invention provides isolation of fecal mucus layer colonocytes. In some embodiments, isolation of fecal mucus layer colonocytes enables detection of the markers of field carcinogenesis. In some embodiments, the majority of epithelial cells in a stool specimen are apoptotic cells. In some embodiments, mucus layer colonocytes are more likely to come from non-tumor colonocytes (e.g., that are abraded from the epithelium as formed stool scrapes against mucosa) than other epithelieal cells in stool. In some embodiments, since the isolated mucus layer colonocytes are non-apoptotic, they provide for detection of field carcinogenesis.

In some embodiments, the present invention provides methods of detecting CRC, pre-CRC, or increased risk of CRC in a subject comprising: (a) isolating colon mucosa from a stool sample from the subject; (b) analyzing colon mucosa for markers or cellular alterations indicative of field carcinogenesis indicative of CRC, pre-CRC, or increased risk of CRC. In some embodiments, colon mucosa comprises mucus layer colonocytes. In some embodiments, the present invention provides methods of detecting CRC, pre-CRC, or increased risk of CRC in a subject comprising: (a) isolating mucus layer colonocytes from a stool sample from the subject; (b) analyzing mucus layer colonocytes for markers or cellular alterations indicative of field carcinogenesis indicative of CRC, pre-CRC, or increased risk of CRC. In some embodiments, mucus layer colonocytes comprise morphologically viable colonocytes. In some embodiments, colon mucosa comprises morphologically viable colonocytes. In some embodiments, colon mucosa comprises non-apoptotic colonocytes. In some embodiments, analyzing colon mucosa comprises analyzing mucus layer colonocytes. In some embodiments, analyzing colon mucosa comprises detection of intracellular nanoarchitectural alterations. In some embodiments, analyzing colon mucosa comprises analysis by partial wave spectroscopy. In some embodiments, analyzing colon mucosa comprises detection of intracellular nanoarchitectural alterations by partial wave spectroscopy. In some embodiments, detection of intracellular nanoarchitectural alterations by partial wave spectroscopy comprises detection of changes in the partial wave spectroscopy parameter Ld. In some embodiments, detection of intracellular nanoarchitectural alterations (e.g., by partial wave spectroscopy) comprises detection of changes either in the spatial refractive index distribution within cells or in the phase shift distribution of light reflected from cells. In some embodiments, detection of intracellular nanoarchitectural alterations (e.g., by partial wave spectroscopy) comprises detection of changes in the statistics of either the spatial refractive index distribution within cells or the statistics of the phase shift distribution of light reflected from cells. In some embodiments, analyzing colon mucosa comprises detecting dysregulation of miRNA expression. In some embodiments, dysregulation of miRNA expression comprises up- and/or down-regulation of expression of one or more miRNA in cells within the colon mucosa. In some embodiments, one or more miRNA comprises miR-34a. In some embodiments, detecting dysregulation of miRNA expression comprises analyzing a panel of miRNA for changes in expression. In some embodiments, detection of markers or alteration indicative of CRC, pre-CRC, or increased risk of CRC provides a diagnosis for the subject. In some embodiments, detection of markers or alteration indicative of CRC, pre-CRC, or increased risk of CRC indicates further testing for the subject. In some embodiments, further testing comprises colonoscopy.

In some embodiments, the present invention provides a method of detecting CRC, pre-CRC, or increased risk of CRC in a subject comprising: (a) isolating colon mucosa from a stool sample from the subject; (b) analyzing the colon mucosa by partial wave spectroscopy; (c) analyzing the colon for dysregulation of miRNA; and (d) diagnosing the subject with CRC, pre-CRC, or increased risk of CRC based on steps (b) and (c). In some embodiments, methods further comprise: (e) providing a subject with a further diagnostic and/or treatment course of action based on step (d). In some embodiments, a further course of diagnostic and/or treatment comprises colonoscopy. In some embodiments, a further course of treatment comprises treating CRC (e.g., surgically, pharmaceutically, other, or combinations thereof).

In certain embodiments, the present invention provides methods of detecting cancer, pre-cancer, or increased risk of cancer in a subject comprising: (a) isolating epithelial cells (e.g., mucosal epithelial cells, non-mucosal epithelial cells, etc.) from a sample from said subject (e.g., from an organ site other than a tumor); (b) analyzing said epithelial cells to detect ultrastructural changes (e.g., changes indicative of field carcinogenesis); (c) analyzing said mucosal epithelial cells for molecular markers of cancer (e.g., markers indicative of field carcinogenesis); and (d) diagnosing said subject with cancer, pre-cancer, or increased risk of cancer based on steps (b) and (c). In some embodiments, methods further comprise providing subject with a treatment course of action based on step (d). In some embodiments, the treatment course of action comprises: surgical treatments, pharmaceutical treatments, other treatments, or combinations thereof. In some embodiments, the mucosal epithelial cells are selected from: colon mucosal cells (e.g., indicative of colon cancer), cervical mucosal cells (e.g., indicative of ovarian cancer), and buccal cells (e.g., indicative of lung cancer). In some embodiments, the ultrastructural changes are detected by a technique selected from: optical detection (e.g., PWS), fluorescence detection, non-optical detection (e.g., electron microscopy), imaging, and super resolution detection. In some embodiments, the ultrastructural changes are detected by optical detection, and said optical detection comprises partial wave spectroscopy. In some embodiments, molecular markers of cancer are selected from: miRNA markers, DNA methylation markers, genetic markers, and epigenetic markers. In some embodiments, molecular markers of cancer comprise dysregulation of miRNA. In some embodiments, the mucosal epithelial cells exhibit ultrastructural changes, but are histologically normal at microscopic or greater scales.

DESCRIPTION OF THE DRAWINGS

FIG. 4 shows a chart of (a) miRNA expression from AOM-treated rat model. (b) Performance of markers from fecal colonocytes at discriminating ADM treatment in rats in pre-neoplastic stage (5 week after AOM treatment).

DETAILED DESCRIPTION OF THE INVENTION

Figure 1:
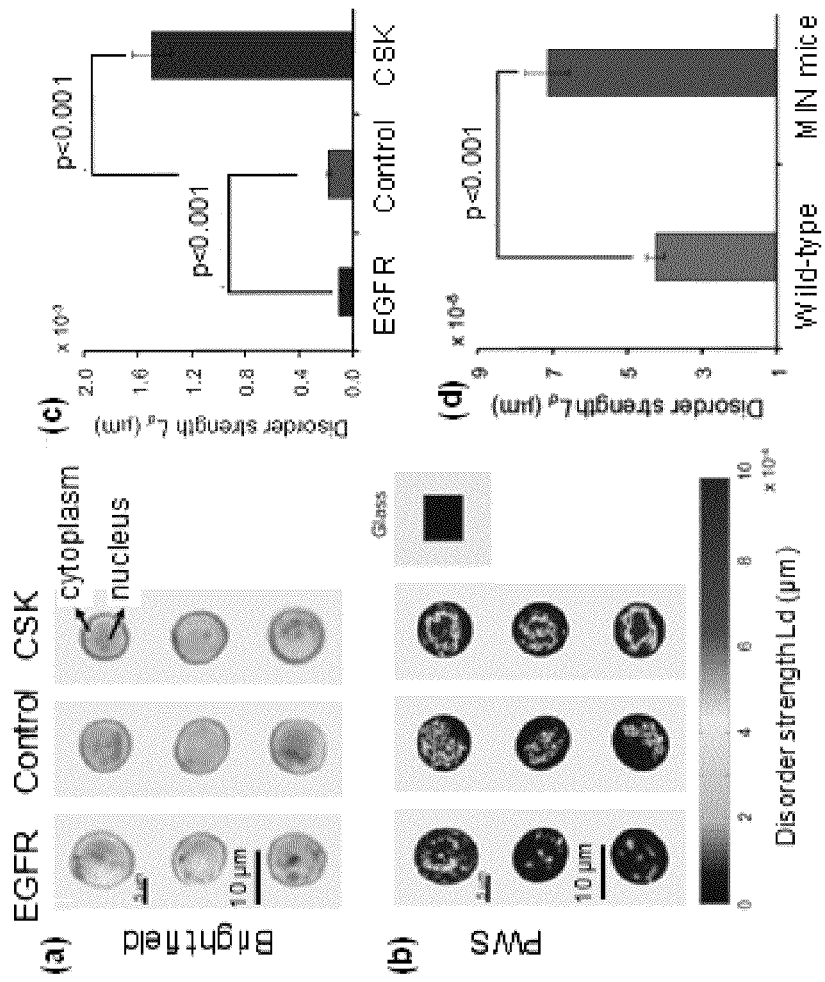
FIG. 1 shows PWS detection of nanoarchitectural alterations. (a-c): Disorder strength of cell nanoarchitecture (Ld) correlates with the neoplastic potential in histologically indistinguishable HT-29 cell lines (EGFR-knockdown, empty vector control, and CSK•knockdown). (d): Ld differences among histologically normal-appearing intestinal cells in the MIN-mouse model of colon cancer. (e): Ld is increased in uninvolved, microscopically normal-appearing colonic cells in the ADM-treated rat model of colon carcinogenesis. (f-i): Ld increase in uninvolved, normal appearing cells is a marker of field carcinogenesis in humans. (f): Lung cancer study (cells obtained from buccal (cheek) mucosa). (g): Pancreatic cancer (duodenal periampullary cells). (h): Ovarian serous cancer: magnitude of Ld increase in cells brushed from the ipsilateral fallopian tube>endometrial cells>cervical cells. (i): Cells at a distance from a colon tumor undergo changes in their internal nanoarchitecture similar to tumor cell. (j) Experimental validation of PWS sensitivity to nanoscale structures (nanostructured models consisting of self-assembled nanospheres of known sizes and refractive index). The linear relationship between Ld measured by PWS and the expected Ld as well as the linear relationship between nanoparticle size Lc and Ld confirm the validity of the PWS analysis.
Figure 1:
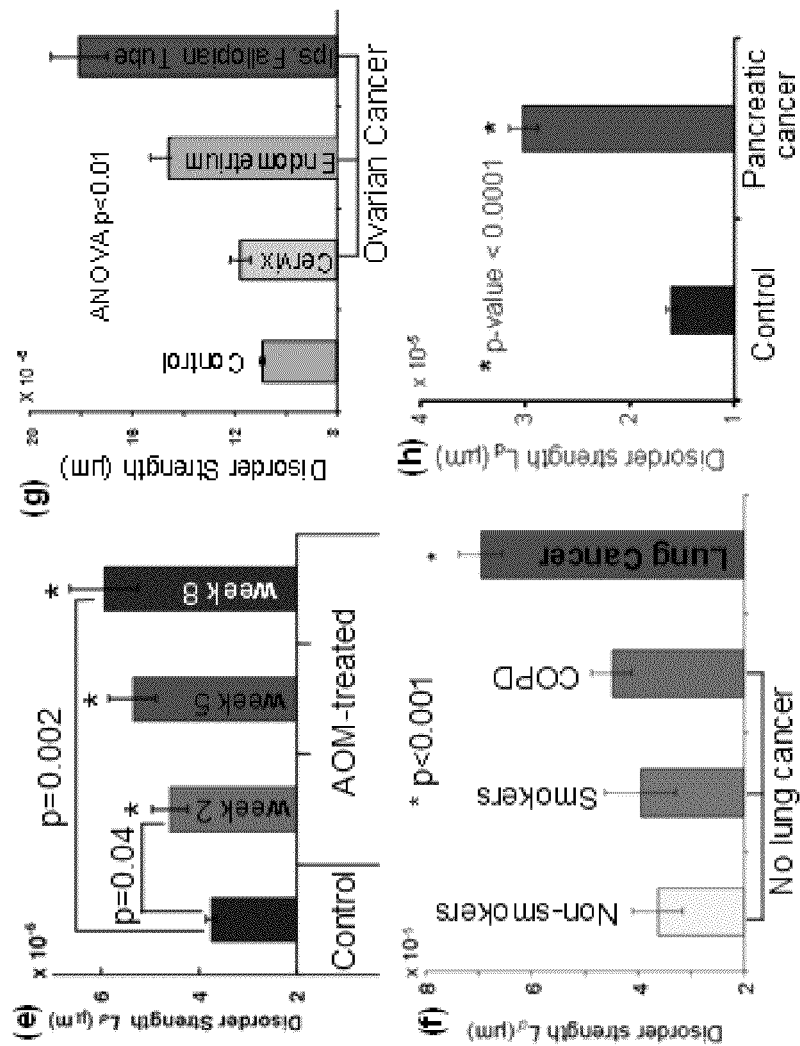
Figure 1:
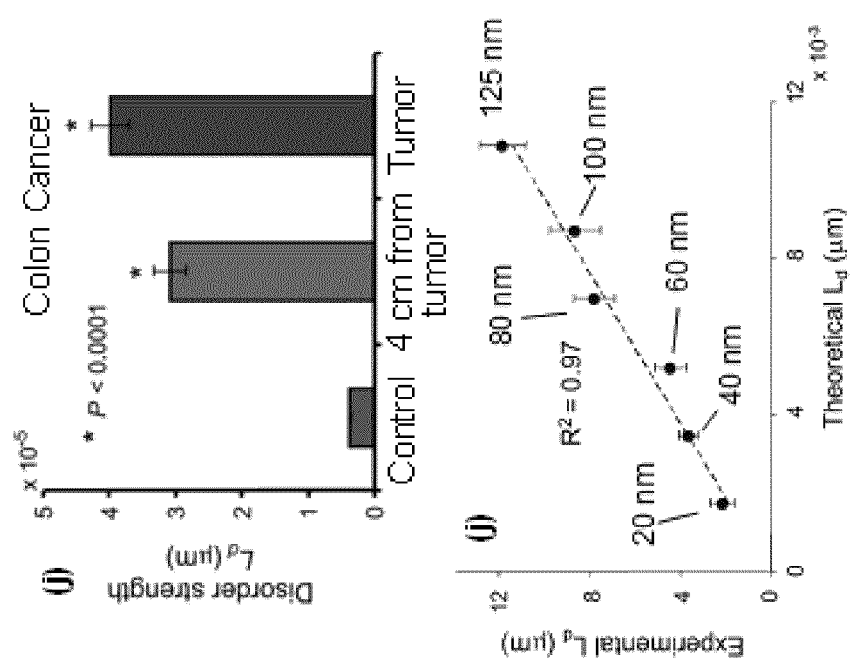

The present invention relates to detection of cancer (e.g., colorectal cancer, ovarian cancer, lung cancer, etc.), or assessment of risk of development thereof. In particular, the present invention provides systems and methods for detection of field carcinogenesis. In some embodiments, the present invention provides compositions and methods for screening a subject for cancer. In some embodiments, the present invention provides examining mucosal material from a subject for indications of cancer, risk for cancer, increased likelihood of cancer, etc. In some embodiments, the present invention provides extracting and/or isolation of mucosal cells (e.g., epithelial cells) from a sample from a subject. In some embodiments, the present invention provides extracting and/or isolation of mucus layer epithelial cells from a biological sample. In some embodiments, the present invention provides a test for cancer screening (e.g., lung cancer screening, colon cancer screening, ovarian cancer screening, etc.). In some embodiments, tests provided herein detect nanoarchitectural (a.k.a. ultrastructural) changes in mucus layer epithelial cells isolated from biological sample. In some embodiments, tests provided herein detect molecular markers of field carcinogenesis in mucus layer epithelial cells isolated from biological sample. In some embodiments, tests are provided to detect both nanoarchitectural (a.k.a. ultrastructural) changes and molecular markers of field carcinogenesis in epithelial cells as a test for cancer screening and diagnosis.

In some embodiments, the present invention provides compositions and methods for screening a subject for colorectal cancer (CRC). In some embodiments, the present invention provides examining fecal matter from a subject for indications of CRC, risk for CRC, increased likelihood of CRC, etc. In some embodiments, the present invention provides extracting and/or isolation of colon mucosa from fecal material. In some embodiments, the present invention provides extracting and/or isolation of mucus layer colonocytes from fecal material. In some embodiments, the present invention provides a fecal test for colon cancer screening. In some embodiments, tests provided herein detect nanoarchitectural changes and molecular markers of field carcinogenesis in mucus layer colonocytes isolated from the stool. In some embodiments, the present invention provides detection of the markers of field carcinogenesis in fecal colonocytes as a test for colorectal cancer screening and diagnosis.

In some embodiments, the present invention provides alternative screening techniques for cancer. For example, the colon cancer screening methods described herein provide alternatives to performing colonoscopy on an entire population. In some embodiments, the present invention provides pre-selecting patients harboring advanced adenomas, the main target of colonoscopy. In some embodiments, pre-selecting patients for colonoscopy (or another screening method for any suitable cancer) allows for focusing finite resources on subjects who will actually benefit from the testing. Colonoscopy is a particularly invasive procedure with finite resources for its performance. Current risk stratification approaches (e.g. flexible sigmoidoscopy, fecal occult blood test) are plagued by unacceptably poor sensitivity and positive predictive value. In some embodiments, the present invention provides a more accurate approach to preselecting patients for current cancer screening techniques (e.g., colonoscopy). In some embodiments, the present invention provides cost-effective, minimally or non-invasive, and easily tolerated cancer (e.g., CRC) screening. In some embodiments, the present invention is used to select patients that would benefit from additional cancer screening (e.g., colonoscopy). In some embodiments, the present invention is a complement additional screening techniques (e.g., standard cancer screening methods, colonoscopy, etc.). In some embodiments, the present invention is an alternative to traditional screening techniques (e.g., standard cancer screening methods, colonoscopy, etc.). In some embodiments, the present invention is a replacement for traditional screening techniques (e.g., standard cancer screening methods, colonoscopy, etc.).

In some embodiments, the present invention provides a risk-stratification approach based on detection of field carcinogenesis. In some embodiments, the present invention provides detection of alterations [e.g. molecular markers (e.g. genetic markers, aberrations in miRNA, epigenetic markers, methylation, etc.) and nanoarchitectural changes] in the genetic/environmental milieu that result in field carcinogenesis (e.g., colon carcinogenesis, lung carcinogenesis, ovarian carcinogenesis). In some embodiments, changes in the genetic/environmental milieu that result in field carcinogenesis also diffusely impact the entire mucosal layer. In some embodiments, the present invention provides detection of alterations [e.g. molecular markers (e.g. miRNA) and nanoarchitectural changes] in the mucosal layer (e.g., colonic mucosa). In some embodiments, the "fingerprint" of risk (e.g., "fertile field") is not limited to cells that comprise an adenoma/tumor, but a much greater number of cells found throughout the mucosal layer. In some embodiments, the "fingerprint" of risk ("fertile field") comprises focal neoplastic lesions determined by stochastic mutations. In some embodiments, numerous molecular biomarkers are altered in the histologically normal mucosa of neoplasia-harboring patients including genomic, proteomic, epigenetic, and biochemical, which, while underscoring the biological plausibility of correlating such alterations with indications of cancer, risk for cancer, or increased likelihood of cancer, lack the requisite sensitivity/specificity for population screening if such alterations are analyzed without further information derived from nanocytological analysis.

In some embodiments, the methods provided herein accurately detect field carcinogenesis by assessing epithelial cells (e.g., colonocytes, buccal cells, cervical epithelial cells, etc.) that were obtained from a biological sample (e.g., stool, pap smear, oral swab, etc.). In some embodiments, the methods assess both structural and molecular facets of cells. In some embodiments, the methods utilize detection of intracellular nanoarchitectural alterations. In some embodiments, intracellular nanoarchitectural alterations are detected using an optical (e.g., PWS), non-optical (e.g., electron microscopy), imaging, fluorescence, or other technology. In some embodiments, intracellular nanoarchitectural alterations are detected using partial wave spectroscopic (PWS) microscopy (U.S. Pat. No. 7,800,746; U.S. Pat. No. 7,667,832; Subramanian et al. Proceedings of the National Academy of Sciences of the United States of America 105(51), 20118-20123 (2008).; Subramanian et al. Optics Letters 34(4), 518-520 (2009).; Subramanian et al. Cancer Research 69(13), 5357-5363 (2009).; herein incorporated by reference in their entireties). In some embodiments, the present invention provides detection of molecular alterations (e.g., genetic alterations, epigenetic alterations, microRNA levels, etc.). In some embodiments, the present invention provides both detection of ultrastructural alterations (e.g., by an optical technique, by a non-optical technique, by PWS, etc.) and the detection of molecular alterations (e.g., genetic alterations, epigenetic alterations, microRNA aberrations (e.g., microRNA levels), etc.). Experiments conducted during development of embodiments of the present invention demonstrated that nanoarchitectural changes (e.g., detected by PWS) and molecular marker aberrations (e.g., microRNA aberrations) can detect potentially developing cancers earlier than other known markers of cancer (e.g., CRC), and therefore provide advantages over other screening methods.

In certain embodiments, the present invention provides methods utilizing PWS (e.g., PWS analysis of fecal colonocytes) and/or molecular marker testing (e.g., microRNA testing) as an initial screening test to determine the need for further cancer screening (e.g., colonoscopy). In some embodiments, the present invention provides an accurate and easily implemented test (e.g., stool test) for detection of cancer, pre-cancer, and/or cancer risk (e.g., CRC, pre-CRC, and/or patient risk of CRC). In some embodiments, the present invention provides cancer screening (e.g., CRC screening) for patients who refuse other testing (e.g., colonoscopy). In some embodiments, the present invention provides cancer screening (e.g., CRC screening) in situations in which other screening (e.g., colonoscopy) is unnecessary. In some embodiments, the present invention provides a screening paradigm that is analogous to the Pap smear-colposcopy paradigm, which has been highly successful relegating cervical cancer from the number 1 to the 14th cause of cancer deaths in women. In some embodiments, systems and methods for cancer (e.g., CRC) screening provided herein provide a replacement for other screening techniques (e.g., colonoscopy).

In some embodiments, the present invention provides methods of screening subjects for cancer (e.g., CRC), or risks thereof, in which: (1) mucus layer epithelial cells (e.g., colonocytes) are isolated from a biological sample (e.g., stool), and (2) markers of field carcinogenesis (e.g., nanoarchitectural, molecular, etc.) are detected. In some embodiments, detection of markers includes, but is not limited to: PWS nanocytology and microRNA analysis. In some embodiments, because field carcinogenesis is a diffuse phenomenon that affects most epithelial cells, a greater number of cells possess these markers (e.g., not limited to cancer cells), and detection is simplified. In some embodiments, the widespread presence of markers detectable by the present invention significantly increases the probability of detecting abnormal cells in a biological sample (e.g., stool), thus dramatically improving the sensitivity of the test, which is a primary limitation of the existing tests.

In some embodiments, the present invention provides isolation mucus layer epithelial cells. In certain embodiments, epithelial cells are obtained by swabbing, brushing, or otherwise physically extracting them from the mucus membrane region of a tissue and/or organ. In some embodiments, sloughed epithelial cells are obtained. In some embodiments, a biological sample (e.g., stool, urine, saliva, blood, etc.) is obtained that contains mucus layer epithelial cells. Detection of the markers of field carcinogenesis is enabled by methods of isolation of mucus layer epithelial cells. In some embodiments, the majority of epithelial cells in a biological sample (e.g., stool specimen, sloughed cells) are apoptotic cells; however, the mucus layer epithelial cells are more likely to come from the normal (e.g., non-tumor) epithelial cells that are abraded from the epithelium. In some embodiments, the mucus layer epithelial cells are non-apoptotic and are uniquely positioned for the detection of field carcinogenesis. In some embodiments, the present invention provides isolation and/or purification of mucus layer epithelial cells. In some embodiments, the present invention provides isolation and/or purification of mucosal epithelial cells. In some embodiments, methods provided herein obtain cells that are abraded from the uninvolved mucosa, not simply sloughed apoptotic cells. In some embodiments, mucosa is collected, isolated, obtained, and/or purified from a biological sample from a subject. In some embodiments, mucus layer epithelial cells are collected, isolated, obtained, and/or purified from a biological sample from a subject. In some embodiments, mucus layer epithelial cells are not cancerous or pre-cancerous, but harbor markers, alterations, and/or signs of cancer, pre-cancer, or an increased cancer risk. In some embodiments, examination of mucosa, isolated by methods of the present invention, allows detection or diagnosis of cancer, pre-cancer, and/or increased risk of cancer. In some embodiments, analysis of mucosal layer epithelial cells allows earlier detection than reliance upon detection of cancerous or pre-cancerous cells.

In particular embodiments, the present invention provides isolation of fecal mucus layer colonocytes. In some embodiments, detection of the markers of field carcinogenesis is enabled by methods of isolation of fecal mucus layer colonocytes. In some embodiments, the majority of epithelial cells in a stool specimen are apoptotic cells; however, the mucus layer colonocytes are more likely to come from the normal (e.g., non-tumor) colonocytes that are abraded from the epithelium as formed stool scrapes against mucosa. In some embodiments, the mucus layer colonocytes are non-apoptotic and are uniquely positioned to detect field carcinogenesis. In some embodiments, the present invention provides isolation and/or purification of mucus layer colonocytes. In some embodiments, the present invention provides isolation and/or purification of colon mucosa. In some embodiments, methods provided herein obtain cells that are abraded from the uninvolved colonic mucosa, not simply the apoptotic cells sloughed into the fecal stream. In some embodiments, colon mucosa is collected, isolated, obtained, and/or purified from a fecal sample from a subject. In some embodiments, mucus layer colonocytes are collected, isolated, obtained, and/or purified from a fecal sample from a subject. In some embodiments, mucus layer colonocytes are not cancerous or pre-cancerous, but harbor markers, alterations, and/or signs of CRC, pre-CRC, or an increased cancer risk in the colon. In some embodiments, examination of colon mucosa, isolated by methods of the present invention, allows detection or diagnosis of CRC, pre-CRC, and/or increased risk of CRC. In some embodiments, analysis of colon mucosa allows earlier detection than reliance upon detection of cancerous or pre-cancerous cells.

In particular embodiments, the present invention provides the use of partial wave spectroscopic microscopy (a.k.a., partial wave spectroscopy (PWS)) for one or more of: detection of cancer, detection of pre-cancer, detection of changes indicative of cancer or pre-cancer, or assessment of risk of having or developing cancer. In some embodiments, the present invention provides the use of partial wave spectroscopic microscopy for one or more of: detection of CRC, detection of pre-CRC, detection of changes indicative of CRC or pre-CRC, or assessment of risk of having or developing CRC. In some embodiments, PWS provides detection of intracellular nanoarchitectural alterations that are indicative or, correlate to, or are diagnostic of: cancer, pre-cancer, and/or risk of developing cancer. In some embodiments, PWS provides detection of intracellular nanoarchitectural alterations that are indicative or, correlate to, or are diagnostic of: CRC, pre-CRC, and/or risk of developing CRC. In some embodiments, the PWS parameter Ld is altered (e.g., increased or decreased) in mucosa (e.g., colon mucosa lung mucosa, ovarian mucosa, etc.), epithelial cells (e.g., colon cells, lung cells, ovarian cells, etc.), epithelial-related cells (e.g., colon-related cells), and/or field carcinogenesis of a subject with cancer (e.g., CRC), pre-cancer (e.g., pre-CRC), and/or at risk of cancer (e.g., CRC). In some embodiments, the present invention provides the detection of intracellular nanoarchitectural alterations in cells that appear normal at the microscopic level. In some embodiments, the present invention provides detecting changes (e.g., increase) in Ld in mucosa (e.g., colon mucosa, lung mucosa, ovarian mucosa, etc.). In some embodiments, alterations in Ld of mucosa (e.g., colon mucosa) is indicative intracellular nanoarchitectural alterations and/or cancerous or pre-cancerous changes (e.g., in the colon and/or intestines). In some embodiments, increase in Ld and/or intracellular nanoarchitectural alterations occur in otherwise normal (healthy)-appearing cells of the mucosal layer (e.g., colon mucosa, lung mucosa, oral mucosa, cervical mucosa, ovarian mucosa, etc.). In some embodiments, cellular and intracellular alterations detected by the compositions and methods of the present invention occur in non-cancerous cells (e.g., of the colorectal region, of the lungs, of the mouth, or the cervix, of the ovaries, etc.), and are not limited to cancerous or pre-cancerous cells. In some embodiments, cellular and intracellular alterations detected by the compositions and methods of the present invention occur in non-cancerous cells (e.g., of the colorectal region, of the lungs, of the ovaries, of the mouth, or the cervix, etc.), and are not limited to cancerous or pre-cancerous cells, thereby allowing early detection of cancer or pre-cancer.

In some embodiments, the present invention provides one or more (e.g., a panel) micro RNAs (miRNA) that are dysregulated (e.g., upregulated or downregulated) in the mucosal layer (e.g., colon mucosa, lung mucosa, ovarian mucosa, etc.), epithelial cells (e.g., lung cells, ovarian cells, colon cells, etc.), epithelial-related cells, and/or field carcinogenesis. In some embodiments, the present invention provides one or more miRNAs (e.g., a panel of miRNAs) that are upregulated in a subject (e.g., in field cariniogenesis and/or mucosal layer cells (e.g., colon mucosa, lung mucosa, ovarian mucosa, etc.) with cancer, pre-cancer, and/or at risk of cancer. In some embodiments, the present invention provides one or more miRNAs that are downregulated (e.g., a panel of miRNAs) in a subject (e.g., in field carcinogenesis and/or colon mucosa) with cancer, pre-cancer, and/or at risk of cancer. In some embodiments, a panel comprises miRNAs that are dysregulated in mucosa (e.g., colon mucosa, lung mucosa, ovarian mucosa, etc.), epithelial cells (e.g., lung cells, ovarian cells, colon cells, etc.), epithelial-related cells, and/or that are indicative of field carcinogenesis of a subject with cancer (e.g., CRC), pre-cancer (e.g., pre-CRC), and/or at risk of cancer (e.g., CRC). In some embodiments, alterations in miRNA expression detected by the compositions and methods of the present invention occur in non-cancerous cells of the region of interest (e.g., colorectal region, lung region, mouth region, cervical region, ovarian region, etc.), and are not limited to cancerous or pre-cancerous cells.

In particular embodiments, cells (e.g., epithelial cells) from the mucosal layer of a tissue/organ proximate to the region being tested for cancer (e.g., mouth for lung cancer, cervix for ovarian cancer, colon for colon cancer) is tested for markers (e.g., molecular markers, ultrastructural markers) that indicate cancer, pre-cancer, or risk of cancer.

In certain embodiments, cells (e.g., epithelial cells) and/or biological samples for analysis by the methods described herein are obtained from mucous membranes or a mucosa of a subject. The present invention is not limited by the type of mucosa. Non-limiting examples of mucosa from which cells or biological samples may be obtained include, but are not limited to: buccal mucosa, esophageal mucosa, gastric mucosa, intestinal mucosa, nasal mucosa, olfactory mucosa, oral mucosa, bronchial mucosa, uterine mucosa, endometrium, colonic mucosa, and/or penile mucosa. The scope of the invention is not limited to cells from mucosa. In some embodiments, methods described herein are used to analyze non-mucosal epithelial cells (e.g., prostate epithelial cells, pancreatic epithelial cells, etc.) In some embodiments, epithelial cells from a biological sample are obtained, isolated, and/or analyzed by the methods described herein. The present invention is not limited by the type of epithelial cells. Non-limiting examples of epithelial cells that find use in embodiments, of the present invention include, but are not limited to: colonocytes, endodermal cells, fallopian tube epidermal cells, mouth epithelial cells, gastric epithelial cells, intestinal epithelial cells, mesothelial cells, germinal epithelial cells, respiratory epithelial cells, olfactory epithelial cells, uroepithelial cells, etc. In certain embodiments, the present invention is not limited to epithelial cells.

In some embodiments, the present invention provides methods of analysis (e.g., of molecular and/or ultrastructural markers) of cells (e.g., epithelial cells) and/or biological samples (e.g., mucosal samples, non-mucosal samples) to detect cancer, pre-cancer, or elevated cancer risk. The scope of the present invention is not limited by the types of cancer that can be detected the methods described herein. Indeed, non-limiting examples of cancers (and the various pre-cancers thereof) are detected in certain embodiments of the present invention include, but are not limited to: bladder cancer, lung cancer, breast cancer, melanoma, colon cancer, rectal cancer, non-Hodgkin's lymphoma, endometrial cancer, pancreatic cancer, renal cell cancer, prostate cancer, leukemia, thyroid cancer, ovarian cancer, cervical cancer, throat cancer, etc.

In some embodiments, the present invention provides methods for the detection of ultrastructural alterations/aberrations in cells, and correlates such alterations/aberrations to cancer, pre-cancer, or a risk thereof. The scope of the present invention is not limited by the methods, means, and/or techniques for detecting, observing, and/or quantitating the cellular nanoarchitecture and/or changes therein. Indeed, non-limiting examples of suitable methods include optical methods (e.g., PWS), non-optical techniques (e.g., electron microscopy), imaging techniques, fluorescence techniques, etc.

EXPERIMENTAL

Example 1

PWS Detection of Nanostructural Alterations in Histological Normal Pre-Neoplastic Cells In experiments conducted during development of embodiments of the present invention, a Sh-RNA approach was used against a tumor suppressor gene, c-terminal src kinase (CSK) and the proto-oncogene, epidermal growth factor receptor (EGFR) in the human colon cancer cell line HT-29. The knockdown was modest (<50%). Thus, the cell lines were microscopically indistinguishable (SEE FIG. 1). However, the PWS parameter Ld was markedly increased (SEE FIG. 1B,C) from the least aggressive cells (EGFR-knockdowns) to intermediate (empty vector) and to the most aggressive (CSK-knockdowns).

Ld increase is a common theme in cells undergoing neoplastic transformation. Ld was markedly increased in the normal-appearing intestinal cells in two different animal models of colon carcinogenesis: the MN-mouse model (model of familiar carcinogenesis, APC mutation; 6 weeks old mice; SEE FIG. 1D) and the azoxymethane (AOM)-treated rats (model of sporadic colon carcinogenesis; 2 weeks after AOM injection; SEE FIG. 1E) well before the appearance of any neoplastic lesions (pre-ACF and preadenoma stage: it takes 20 weeks for adenomas to develop, with carcinomas taking 35 weeks). Although genetic and epigenetic events in field carcinogenesis have been previously studied, it had been assumed that cells are morphologically normal. Experiments conducted during development of embodiments of the present invention show that these cells do possess morphological alterations, although not at the microscale but at the nanoscale, the length scale of macromolecular structures and other fundamental building blocks of the cell.

Experiments were conducted during development of embodiments of the present invention to examine nanoarchitectural alterations in colon field carcinogenesis (Subramanian, Cancer Research 69(13), 5357-5363 (2009); herein incorporated by reference in its entirety). Given that Ld is increased early in carcinogenesis, experiments were conducted to assess whether Ld would be altered in both tumor cells and in histologically normal colonic cells in the field carcinogenesis. Cells were brushed via a standard protocol with a cyto-brush, transferred onto a glass slide, ethanol-fixed, and confirmed to be histologically normal by a cyto-pathologist. Randomly chosen cells were analyzed by PWS for each patient by an operator blinded to the diagnosis. For each cell, PWS generates a "heat-map" Ld-image (SEE FIG. 1B). We calculated the mean Ld for each cell. The average of this mean gives the patient-mean Ld.

Experiments conducted during development of embodiments of the present invention established that Ld is increased in tumor cells compared to age and gender matched normal controls. Ld was significantly elevated in the tumor cells (SEE FIG. 1J); histologically normal cells 4 cm from the tumor (field carcinogenesis) also had an increased Ld (SEE FIG. 1J). Thus, although appearing normal by the criteria of histopathology, these cells possess alterations in their nanoarchitecture.

Figure 2:
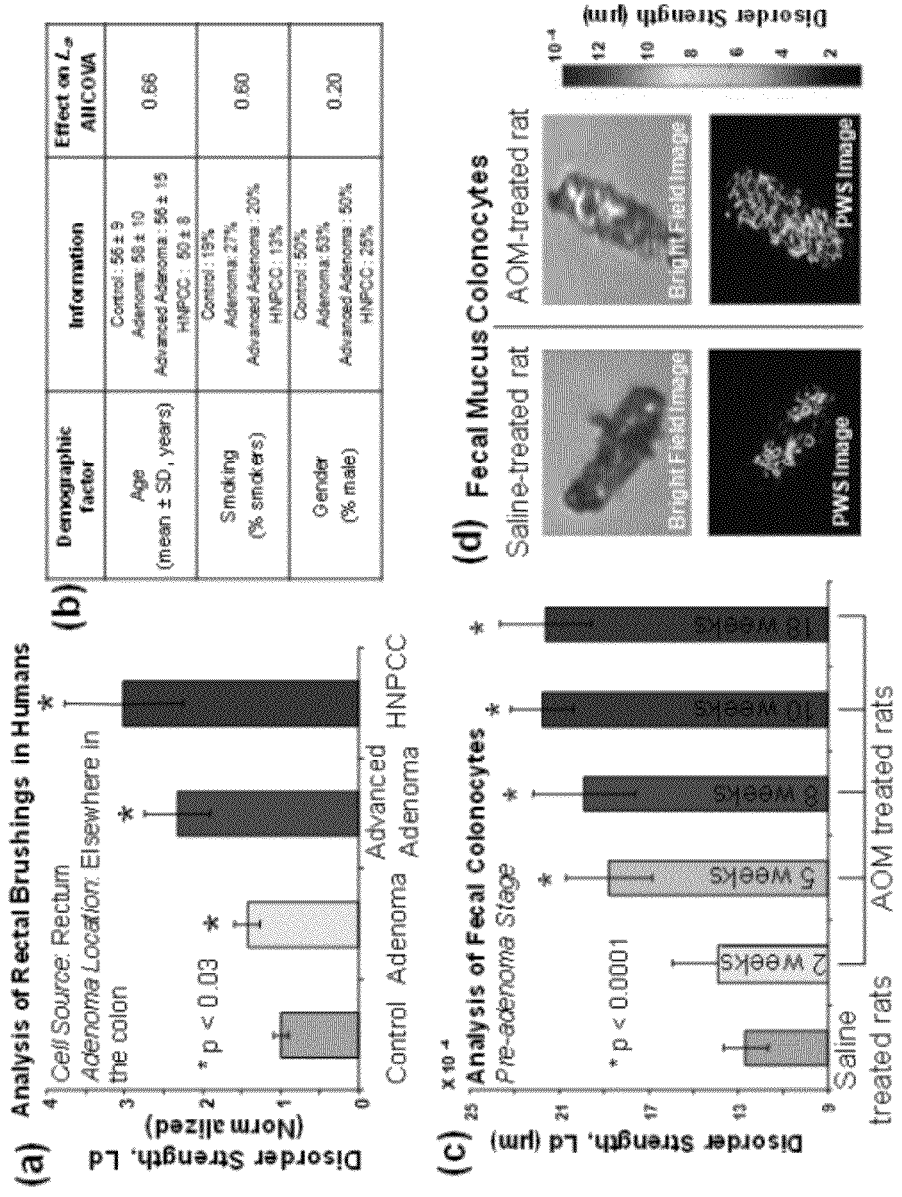
FIG. 2 shows (a) Ld is elevated in histologically normal cells in patients with adenomas and HNPCC. The magnitude of Ld increase parallels CRC risk. (b) Demographic and risk factors do not confound PWS diagnosis. (c) PWS analysis of fecal mucus colonocytes in the AOM•treated rat model of CRC. Ld is increased in AOM-treated and progresses over time after the ADM treatment, thus paralleling the progression of carcinogenesis. (d) Microscopic and PWS images of representative fecal colonocytes.

Ld is increased in histologically normal cells in field carcinogenesis. Rectal brushings from the endoscopically and histologically normal mucosa were performed on patients undergoing colonoscopy: control patients with no neoplasia, patients with non-advanced adenomas, patients with advanced adenomas, and patients with HNPCC (hereditary nonpolyposis colorectal cancer syndrome). There was a progressive increase in rectal Ld that correlated with the magnitude of neoplasia: no neoplasia patients<patients with non-advanced adenomas (most of which spontaneously regress) <patients with advanced adenomas (a more aggressive precancerous lesion)<HNPCC patients (highest risk of progression to cancer) (SEE FIG. 2). The effect was significant for all groups.

Experiments conducted during the development of embodiments of the present invention demonstrated that performance of Ld for concurrent neoplasia was excellent. The area under the ROC curve (AUC) for a single marker (Ld) was 0.900 for carcinomas, 0.863 for advanced adenomas and 0.779 for all adenomas. Ld increase is not confounded by demographic and risk factors. Patients' demographic and risk factors (e.g., age, smoking history, and gender) did not have an effect on either values of Ld or diagnostic outcome with ANCOVA p-values of 0.66, 0.60, and 0.20, respectively (SEE FIG. 2b). The correlation analysis further confirmed the non-significant association between the demographic factors and Ld. Finally, cases and controls were age, gender and smoking history matched (SEE FIG. 2B).

Experiments conducted during the development of embodiments of the present invention demonstrated that PWS is sensitive to distal and proximal adenomas. Adenomas were uniformly distributed among colonic segments (53% distal, 47% proximal), and there was no difference between rectal Ld in patients with distal vs. proximal neoplasia.

Experiments conducted during the development of embodiments of the present invention demonstrated no effect of benign colon pathology. 22% of adenoma-free patients had benign lesions (e.g., diverticuli, hyperplastic polyps), and Ld was not altered in these patients (ANOVA). However, an Ld increase was shown to be sensitive to future neoplasia. PWS was performed on histologically normal rectal cells in patients with a high risk of neoplasia, i.e., hereditary nonpolyposis colorectal cancer (HNPCC) syndrome (germline mutation in genes hMLH1 and hMSH2), which portends a very high lifetime risk of CRC. Although these patients did not have concurrent adenomas, the rectal Ld was markedly altered (SEE FIG. 2A). Indeed, Ld was higher in HNPCC patients than in patients with concurrent advanced adenomas consonant with the relative lifetime risk: 60-80% vs. 2-5% per year, respectively (Lynch and de la Chapelle. N Engl J Med 348(10), 919-932 (2003).; Brenner et al. Gut 56(11), 1585-1589 (2007).; herein incorporated by reference in their entireties).

Example 2

Mucus Layer Fecal Colonocyte Isolation

Fecal colonocyte isolation techniques are typically laborious and cumbersome (Matsushita et al. Gastroenterology 129 (6), 1918-1927 (2005).; herein incorporated by reference in its entirety). Recently, a new assay focusing on the mucus layer was developed, which is advantageous with regards to practicality while offering a good and reliable yield of cells (White et al. Cancer Epidemiol Biomarkers Prev 18(7), 2006-2013 (2009).; herein incorporated by reference in its entirety). By using the mucus layer, cells that are abraded from the uninvolved colonic mucosa related to stool passage are targeted, rather than simply the apoptotic cells sloughed into the fecal stream. The protocol is follows: stool (e.g., refrigerated, delivered within 12 hours of defecation) is washed with chilled 0.5% ammonium thioglycolate solution (Sigma Aldrich) prepared in PBS, gently agitated and centrifuged at 800 rpm for 5 min at 4° C. The pellet is resuspended in PreservCyt solution (Hologic), and incubated for 45 min. Samples are filtered through a 300 µm filter mesh (Nasco Whirl-Pak) to remove large debris followed by filtering through a 125 µm polypropylene mesh (Small Parts, Inc). The retained solids (including the mucus layer colonocytes) are washed with the ammonium thioglycolate solution, centrifuged at 800 rpm for 5 min at 4° C. and the top layer is extracted. The samples are then centrifuged at 800 rpm for 5 min at 4° C. Supernatant is removed and fresh 0.5M N-acetyl L-cysteine (Sigma-Aldrich) in PBS is added. 0.5 mUg of original stool sample along with 1.5 mM EDTA and samples is rotated at 37° C. at 150 rpm for 10-15 min. The samples are diluted with PreservCyt to 18-20 mL and cells are applied on glass slides using ThinPrep 2000 Processor (Hologic) or placed in TRIzol for microRNA analysis.

Figure 3:
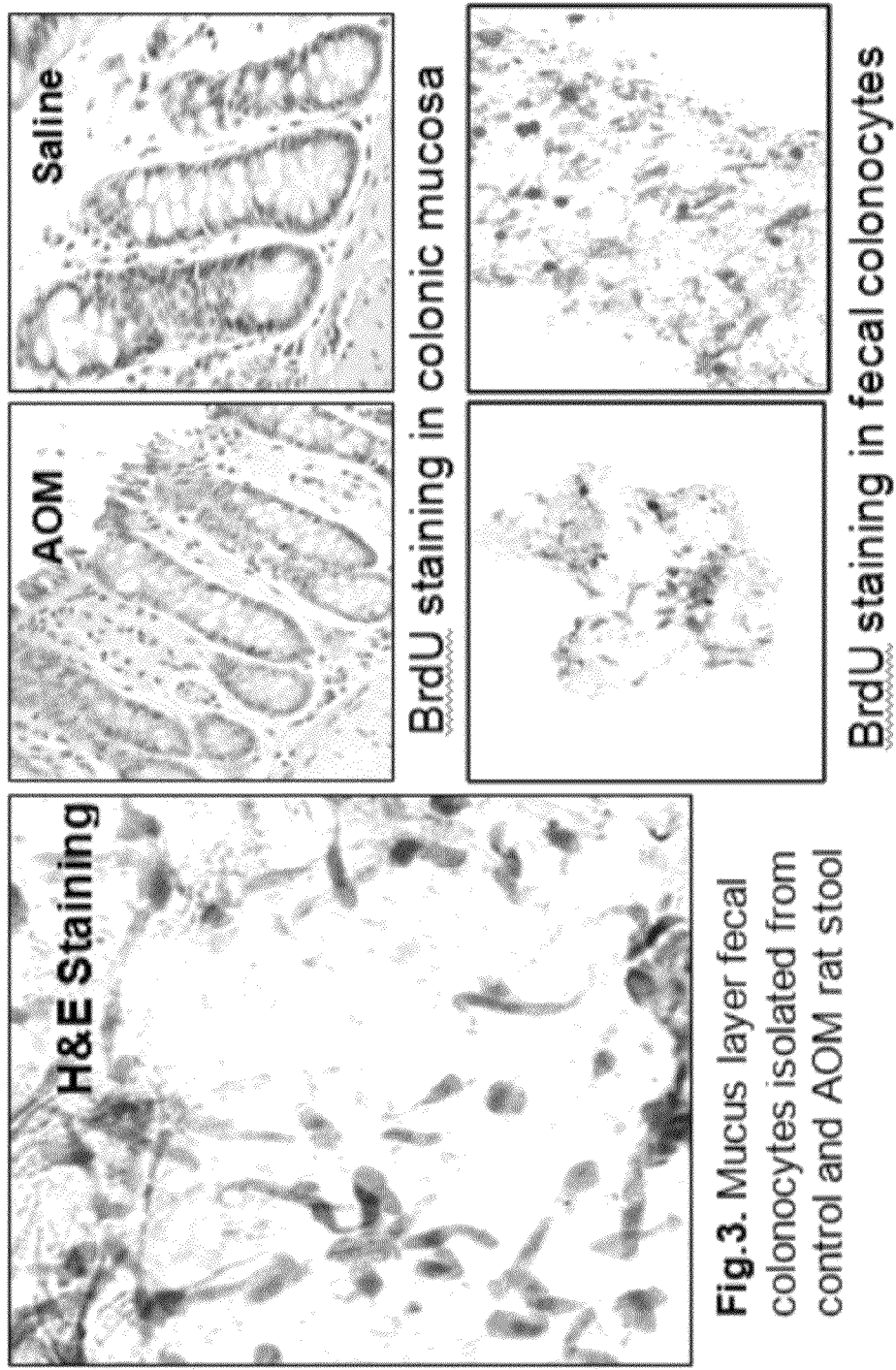
FIG. 3 shows images of mucus layer fecal colonocytes isolated from control and ADM rat stool.

Experiments were conducted during development of embodiments of the present invention to test the above protocol using the AOM-treated rat model. A typical colonocyte (SEE FIG. 3) was confirmed by specific cytokeratin immunoreactivity patterns. To elucidate the origin of mucus layer colonocytes, rats were injected with BrdU (which labels proliferating cells at the base of the crypt that migrate upwards over time) and then sacrificed 24 hours later. Prior to sacrifice, fecal colonocytes were assessed. Data showed that i) 10-20% of the fecal colonocytes were labeled with BrdU yet none of the cells was in the upper half of the crypt (those that are progressing to being sloughed off by apoptosis), and ii) none of the mucus layer fecal colonocytes demonstrated cleaved caspase 3 immunoreactivity (marker of apoptosis). This proves that mucus layer colonocytes were obtained through mechanical abrasion of passage of formed stool (thus representing field carcinogenesis), and not through the apoptosis of colonocytes at the top of the crypt, which are generally found in the center of the stool bolus. To address the issue of whether the detection of field carcinogenesis via fecal colonocytes, studies were performed on saline versus AOM-treated rats, and it was noted that the effect size of miRNA dysregulation for the mucus colonocytes assay was twice that seen with simple stool homogenate. Effect size of a marker is defined as the difference between the mean marker's value for the cases and controls normalized by the cumulative standard deviation of the marker.

Example 3

PWS Detects Nanoarchitectural Alterations in Fecal Colonocytes in a Rat Model of CRC Experiments were conducted using stool from AOM-treated vs. age-matched saline-treated rats. In this model, adenomas and carcinomas develop 20 and 35 weeks after AOM injection, respectively. For PWS analysis, 218 week post-carcinogen-injection time-points were chosen to replicate the human field carcinogenesis condition. After extraction, fecal colonocytes were placed in a cytokine solution (a method based fixative) after which a cytology slide was made using ThinPrep 2000 machine (Cytec). The yield of PWS analyzable cells was 15 cells/g of aliquot. Statistically and diagnostically significant results are observable with 20-30 cells per patient; therefore, as little as ~2 g of aliquot is sufficient to perform PWS on fecal colonocytes. FIG. 2(D) shows representative Ld-images from fecal colonocytes obtained from saline and AOM-treated rats. A shift towards higher values of Ld can be appreciated. Ld was increased at week 5 for AOM-treated rats compared to the age-matched controls and continued progressively increase for later time points in parallel to the progression of carcinogenesis in the rat model. AUC for AOM vs. saline-treated rats for 5 weeks post AOM-treatment was excellent at 0.877 when Ld values from 3 randomly chosen cells were averaged. AUC improved to 0.928 (100% sensitivity, 75% specificity) for the 10 week time point.

Example 4

MicroRNA Profiling in Colonic Field Carcinogenesis

Fisher 344 rats were given two Lp injections of either saline or AOM (15 mg/kg, Sigma). Total RNA was isolated from the uninvolved colonic tissue and tumors and the RNA was processed for miRNA microarray analysis (>300 miRNAs array, Agilent G2565 Scanner with Feature Extraction & GeneSpring GX v7.3.1). Comparative analysis of the differential miRNA expression during colon carcinogenesis was performed (SEE FIG. 3A; increase and decrease defined as >1.5 or <0.67 fold, respectively). In the uninvolved mucosa, treatment with the established chemopreventive agent caused 16 microRNAs to be altered supporting the central nature of microRNA in early colon carcinogenesis (pre-dysplastic mucosa). This was in humans with a 760 microRNA of two predefined Megaplex RT Primer pools (taq man probes) gene card microarrays (Applied Biosystems) performed on the microscopically normal mucosa of patients with CRC compared to those resected for non-neoplastic indications (predominantly diverticulosis). In the microscopically normal mucosa, 26 and 88 microRNAs were statistically significantly up and down-regulated, respectively.

Example 5

MicroRNA Modulation in Mucus Layer Fecal Colonocytes

As discussed above, mucus layer fecal colonocytes are representative of field carcinogenesis, and in the AOM-treated rat model and humans microRNAs are dysregulated in field carcinogenesis. In experiments conducted during the development of embodiments of the present invention, microRNAs were isolated from fecal colonocytes (via TRIzol reagent, Molecular Research Labs). Four out of six microRNAs observed were upregulated. For example, 4.4-fold induction in upregulation of miR-34a was observed in fecal colonocytes. This was equivalent to the induction in the histologically normal mucosa (4.6 fold) but less than found in tumors (28.9 fold), further arguing that mucus layer fecal colonocytes were derived from abraded cells.

Example 6

Diagnostic Performance of PWS and MicroRNA from Fecal Colonocytes

Stool was isolated from AOM-treated rats at 5 weeks postcarcinogen treatment (prior to adenoma development). PWS was performed on isolated fecal mucosal colonocytes to evaluate the nanoarchitectural characteristics of the cells, and real time PCR were performed to assess the levels of miR34a. Even at this early time point, AUC was outstanding (SEE FIG. 4B). Clear synergism was observed from these two different marker categories for field carcinogenesis. These data demonstrate that microRNA+PWS is a powerful diagnostic combination.

Example 7

Detection of Multiple Cancer Types by PWS

Field carcinogenesis has been reported in multiple cancer types (Kopelovich et al. Clin Cancer Res 5(12), 3899-3905 (1999).; Dakubo et al. Cancer Cell International 7(2)(2007).; herein incorporated by reference in their entireties). Experiments conducted during the development of embodiments of the present invention demonstrate that Ld increase is a universal phenomenon in carcinogenesis. For example, Ld increase in histologically normal buccal cells was able to distinguish among patients with lung cancer from the controls (matched by age and tobacco exposure) who were neoplasia-free (SEE FIG. 1F). The data were not confounded by age or the amount of smoking Likewise, when cells were brushed cells from the histologically normal periampullary duodenal mucosa, Ld was increased in pancreatic cancer patients over those without pancreatic cancer (SEE FIG. 1H). The most aggressive serous subtype of ovarian cancer (~80% of malignancies) initially develops not in the ovary but in the fimbrae of the fallopian tubes. Therefore, fallopian tubes and endometrium were assessed, and there was a significant increase in Ld in these histologically normal epithelia in patients with serous ovarian cancer versus age-matched neoplasia-free patients (SEE FIG. 1G).

Example 8

Synergy of Ultrastructural and Molecular Markers

Experiments conducted during development of embodiments of the present invention demonstrate that the combination of ultrastructural and molecular markers performs better at detecting cancer than these individual markers alone.

Experiments conducted during development of embodiments of the present invention demonstrate a correlation between cancer and nanoarchitectural alterations in cells, as assayed by the increase in the disorder strength measured by PWS. While the present invention is not limited by the means of detecting nanostructural alterations, experiments have demonstrated that the optical spectroscopic microscopy technique, PWS, is particularly useful for assessing cellular architecture and correlating it to cancer. It should be noted that other techniques that measure or image cell structure at submicron scale, such as various modalities of electron microscopy, find use in embodiments described herein.

Experiments conducted during development of embodiments of the present invention demonstrate a correlation between cancer and microRNA alterations. However, the present invention is not limited by the type of molecular markers, and synergy between ultrastructural alterations and other types of molecular markers is within the scope of the present invention. Examples of molecular marker candidates that can be synergetic to the ultrastructural markers include methylation, epigenetic markers, gene products, etc. The synergy between molecular (e.g., microRNA) and ultrastructural (e.g., optical) markers is not limited to field carcinogenesis in the colon. Instead, experiments conducted during development of embodiments of the present invention demonstrate this synergy is indicative of a more universal cancer phenomenon. In addition to experiments conducted on colon mucosal cells, experiments have been conducted during development of embodiments of the present invention demonstrating synergy between the two types of markers in both lung and ovarian cancers.

Figure 5:
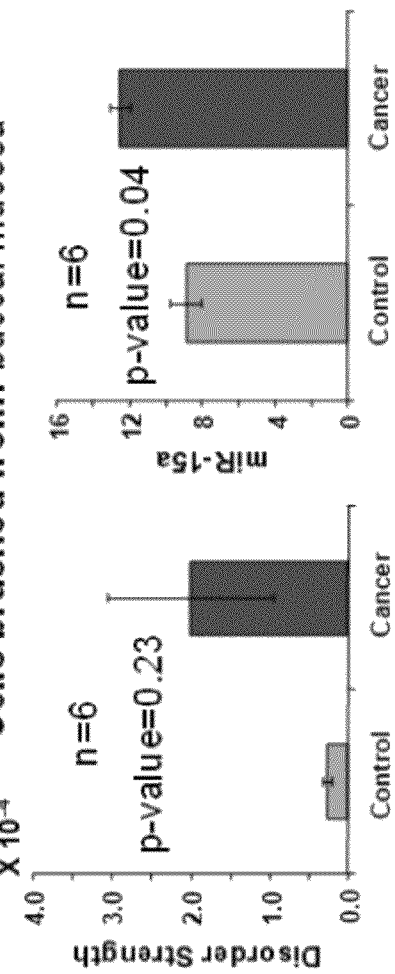
FIG. 5 shows molecular (microRNA) and ultrastructural (optical) markers of lung cancer obtained from buccal cells are synergistic.

Experiments demonstrate that field carcinogenesis of lung cancer can be found in the oral cavity (buccal mucosa). Cells were brushed from the buccal mucosa in patients with and without lung cancer. Ld increase in buccal cells is diagnostic for lung cancer (SEE FIG. 1F). In a subset of the patients, both PWS and microRNA analysis were performed on the brushed cells. In addition to Ld elevation in patients with lung cancer, a number of microRNA levels were also altered, including miR-16 (decreased), miR-21 (decreased), miR-31 (decreased), and miR-15a (increased). Experimental data demonstrates that miR-15a was upregulated in patients with lung cancer (SEE FIG. 5). In these patients, the disorder strength of the buccal cells was also increased (SEE FIG. 5). Both miR-15a and Ld showed 100% separation between the cancer and control groups. A correlation coefficient between Ld and miR-15a was 0.45, which confirmed these two markers were not a mere replica of each other but are indeed synergistic.

Experiments were also conducted during development of embodiments of the present invention to detect field carcinogenesis in the fallopian tubes and the endometrium (SEE FIG. 1G). Ld was elevated in epithelial cells brushed from the endometrium and the fallopian tubes.

Figure 6:
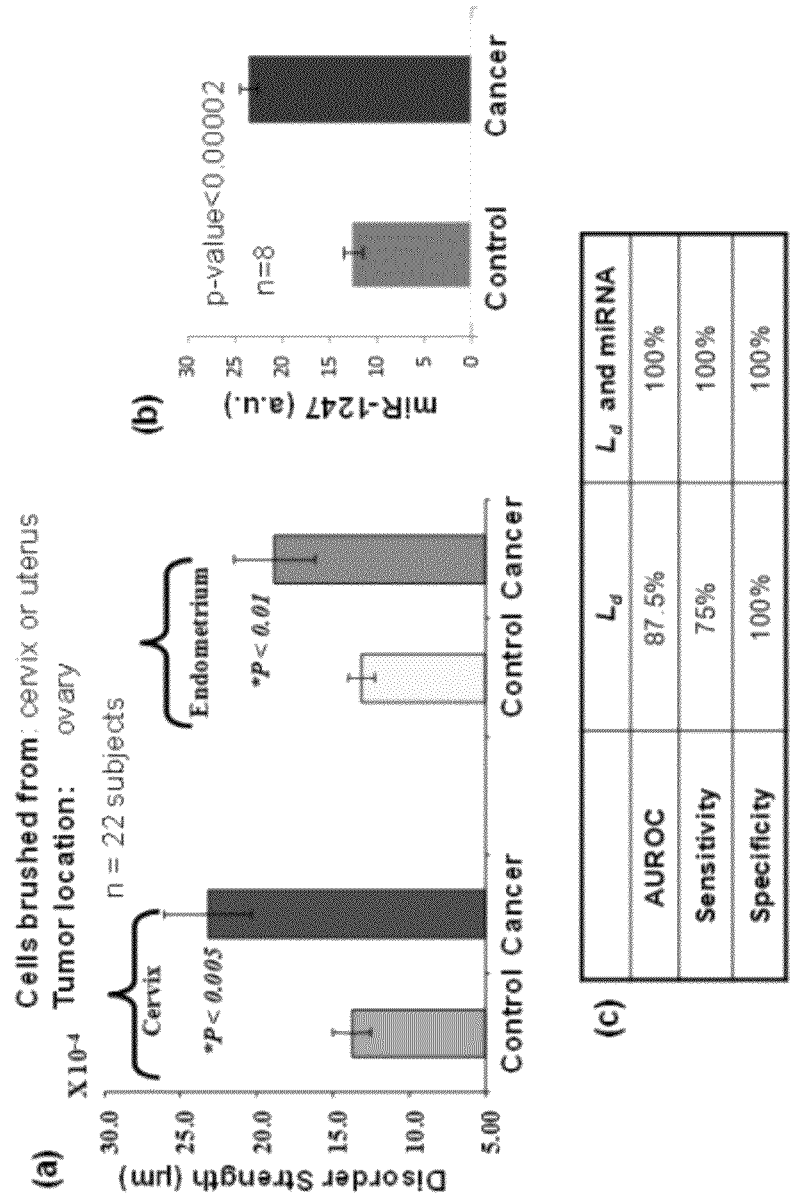
FIG. 6 shows (a) ovarian field carcinogenesis can be detected from cervical epithelial cells; and (b) molecular (microRNA) and ultrastructural (optical) markers of ovarian cancer obtained from cervical cells are synergistic.

There have been no studies prior to the experiments conducted during development of embodiments of the present invention demonstrating that field carcinogenesis can be found in cervical cells. In experiments conducted during development of embodiments of the present invention, cells were brushed from the cervical mucosa in patients with and without ovarian cancer. Ld measured in these cells was markedly and significantly elevated in patients with ovarian cancer (SEE FIG. 6A). The sensitivity and specificity of Ld increase in cervical cells as a marker of ovarian cancer were excellent: 86.11% and 80.36%, respectively. This demonstrates that not only field carcinogenesis associated with ovarian cancer exists in the cervix but also that it is detectable by means of PWS, potentially enabling ovarian cancer detection and screening. In a subset of the patients both PWS and microRNA analysis were performed on the brushed cervical cells. A number of microRNAs were upregulated in patients with ovarian cancer including miR-1247, miR-144, miR-187, and miR-18a. In these patients, the disorder strength of the cervical cells was also increased. While, in this subset of patients, the sensitivity and specificity of PWS were 87.5% and 75%, respectively, when combined with either miR=1247 or miR-187, the diagnostic performance increased to a perfect 100% sensitivity and specificity. A correlation coefficient between Ld and miR-1247 was 0.83, which confirmed these two markers were not a mere replica of each other but are indeed synergistic.

Example 9

Exemplary Cancer Screening Procedure

In some embodiments, the combination of molecular and ultrastructural markers provide a synergistic effect that can be used for cancer diagnosis and screening. In some embodiments, the combination of molecular and ultrastructural markers provides enhanced cancer detection over either marker alone. In some embodiments, cancer screening using the methods described herein is carried out according to the following protocol, or variation thereon. Those of skill in the art will recognize suitable variations of this procedure. Moreover, the scope of the present invention is not limited by such a procedure.

A cellular specimen is obtained by means of brushing (e.g., buccal brushings for lung cancer screening, cervical brushings for ovarian cancer screening, etc.), from secretions, or from other byproducts (e.g., fecal colonocytes for colon cancer screening). Ultrastructural analysis is performed on a portion of the extracted cells to identify markers of neoplasia from an ensemble of the extracted cells. Such analysis can be performed by an optical (e.g., PWS) or a non-optical technique (e.g., electron microscopy). Another portion of the extracted cells is subjected to molecular (e.g. microRNA) analysis. When the two types of markers are determined independently, the results are combined into a unified prediction rule. In experiments conducted during development of embodiments of the present invention using fecal colonocytes for colon cancer screening, buccal cells for lung cancer screening, and cervical cells for ovarian cancer screening, a common prediction rule was developed based on a linear regression where a value of a ultrastructural marker (e.g., disorder strength) is summed with a value of a molecular marker (e.g., level of a particular diagnostic microRNA). The sum was the combined marker. Alternatively, a tree-based prediction rule can be used where the diagnostic decision is made by comparing the values of one of the markers first (e.g., ultrastructural marker). If the value is above or below a set cut off, the molecular marker is considered to further refine the diagnosis. The synergy between the two types of markers has two facets: i) improved diagnostic performance and ii) both types of markers can be identified based on the same specimen (e.g., brushed cells) with no additional specimen collection required.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A method of detecting colorectal field carcinogenesis in a subject comprising:
   (a) isolating mucus layer colonocytes from a stool sample from said subject, wherein said mucus layer colonocytes are histologically normal at microscopic and greater scales;
   (b) analyzing said mucus layer colonocytes for nanoscale morphological alterations indicative of field carcinogenesis, wherein said nanoscale morphological alterations manifest as an increase in disorder strength as measured by partial wave spectroscopy but are not observable at the microscopic and greater scales.

2. The method of claim 1, wherein said colon mucosa comprises non-apoptotic colonocytes.

3. The method of claim 1, wherein analyzing said mucus layer colonocytes for nanoscale morphological alterations comprises detection of changes in spatial refractive index distribution within cells or the phase shift distribution of light reflected from cells.

4. The method of claim 1, wherein analyzing said mucus layer colonocytes for nanoscale morphological alterations comprises analysis by partial wave spectroscopy.

5. The method of claim 4, wherein analyzing said mucus layer colonocytes for nanoscale morphological alterations by partial wave spectroscopy comprises detecting an increase in disorder strength.

6. The method of claim 1, further comprising analyzing said mucus layer colonocytes molecular markers of cancer indicative of field carcinogenesis.

7. The method of claim 6, wherein molecular markers of cancer indicative of field carcinogenesis are selected from dysregulation of miRNA expression, alterations in DNA methylation, and epigenetic markers.

8. The method of claim 7, wherein dysregulation of miRNA expression comprises dysregulation of miR-34a expression.

9. The method of claim 7, wherein detecting dysregulation of miRNA expression comprises analyzing a panel of miRNA for changes in expression.

10. The method of claim 1, wherein detection of colorectal field carcinogenesis indicates further testing of said subject.

11. A method of detecting cancer, pre-cancer, or increased risk of cancer in a subject comprising:
   (a) isolating epithelial cells from a sample from said subject, wherein said epithelial cells are histologically normal at microscopic and greater scales;
   (b) having said epithelial cells analyzed to detect nanoscale morphological alterations that manifest as an increase disorder strength as measured by partial wave spectroscopy but are not observable at the microscale;
   (c) having said epithelial cells analyzed to detect for molecular markers of cancer indicative of field carcinogenesis, wherein said molecular markers are selected from: dysregulation of miRNA expression, alterations in DNA methylation, and epigenetic markers; and
   (d) diagnosing said subject with cancer, pre-cancer, or increased risk of cancer based on steps (b) and (c).

12. The method of claim 11 further comprising:
   (e) providing subject with a treatment course of action based on step (d).

13. The method of claim 12, wherein the treatment course of action comprises: surgical treatments, pharmaceutical treatments, or combinations thereof.

14. The method of claim 11, wherein said epithelial cells are selected from: colon mucosal cells, cervical mucosal cells, and buccal cells.

15. The method of claim 11, wherein said nanoscale morphological alterations are detected by a technique selected from: optical detection, fluorescence detection, non-optical detection, imaging, and super resolution detection.

16. The method of claim 15, wherein said nanoscale morphological alterations are detected by optical detection, and said optical detection comprises partial wave spectroscopy.

* * * * *